US010701847B2

(12) United States Patent
Kato

(10) Patent No.: US 10,701,847 B2
(45) Date of Patent: Jun. 30, 2020

(54) ELECTROMAGNETIC WAVE SHIELDING MATERIAL, BUILDING MATERIAL WITH ELECTROMAGNETIC WAVE SHIELD, AND ARTICLE WITH ELECTROMAGNETIC WAVE SHIELDING MATERIAL

(71) Applicant: Murata Manufacturing Co., Ltd., Nagaokakyo-shi, Kyoto-fu (JP)

(72) Inventor: Noboru Kato, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 16/281,411

(22) Filed: Feb. 21, 2019

(65) Prior Publication Data
US 2019/0191599 A1 Jun. 20, 2019

Related U.S. Application Data

(63) Continuation of application No. PCT/JP2018/003107, filed on Jan. 31, 2018.

(30) Foreign Application Priority Data

Apr. 11, 2017 (JP) ................... 2017-078294

(51) Int. Cl.
*H05K 9/00* (2006.01)
*H03H 1/00* (2006.01)
(Continued)

(52) U.S. Cl.
CPC ........... *H05K 9/0081* (2013.01); *A61B 5/055* (2013.01); *B32B 7/02* (2013.01); *E04B 1/92* (2013.01);
(Continued)

(58) Field of Classification Search
CPC ... H05K 9/0075; H05K 9/0081; H05K 9/0094
See application file for complete search history.

(56) References Cited

U.S. PATENT DOCUMENTS 6,147,302 A 11/2000 Matsuo et al.
7,495,181 B2 * 2/2009 Matsushita ............ H01Q 17/00
174/377
(Continued)

FOREIGN PATENT DOCUMENTS

JP H1168374 A 3/1999
JP H11204984 A 7/1999
(Continued)

OTHER PUBLICATIONS

International Search Report issued for PCT/JP2018/003107, dated Apr. 17, 2018.
Written Opinion of the International Searching Authority issued for PCT/JP2018/003107, dated Apr. 17, 2018.

*Primary Examiner* — Hung V Ngo
(74) *Attorney, Agent, or Firm* — Arent Fox LLP

(57) ABSTRACT

An electromagnetic wave shielding material is provided that is configured to prevent a usage environment from being limited. The electromagnetic wave shielding material shields an electromagnetic wave having a frequency, and includes a substrate and a plurality of resonance loops disposed on the substrate. Moreover, the plurality of resonance loops are positioned on the substrate to be magnetically coupled to each other. Each of the resonance loops forms an LC parallel resonance circuit that resonates at the frequency of the electromagnetic wave.

20 Claims, 16 Drawing Sheets

(51) Int. Cl.
*B32B 7/02* (2019.01)
*E04B 1/92* (2006.01)
*A61B 5/055* (2006.01)
*H05B 6/76* (2006.01)
*E06B 5/18* (2006.01)
*B32B 17/06* (2006.01)

(52) U.S. Cl.
CPC .............. *H03H 1/00* (2013.01); *H05B 6/76* (2013.01); *H05K 9/0003* (2013.01); *H05K 9/0005* (2013.01); *H05K 9/0094* (2013.01); *B32B 17/064* (2013.01); *B32B 2255/10* (2013.01); *B32B 2255/20* (2013.01); *B32B 2307/212* (2013.01); *B32B 2419/00* (2013.01); *E04B 2001/925* (2013.01); *E06B 5/18* (2013.01); *H03H 2001/0021* (2013.01)

(56) References Cited

U.S. PATENT DOCUMENTS

| | | | |
|---|---|---|---|
| 2002/0015293 | A1* | 2/2002 | Akiba ................ H01L 23/5383 361/793 |
| 2012/0212395 | A1 | 8/2012 | Sanada |
| 2015/0229031 | A1 | 8/2015 | De Lustrac et al. |

FOREIGN PATENT DOCUMENTS

| | | |
|---|---|---|
| JP | 2007180114 A | 7/2007 |
| JP | 2012175522 A | 9/2012 |
| JP | 2015534760 A | 12/2015 |
| WO | 9835542 A1 | 8/1998 |

\* cited by examiner

ELECTROMAGNETIC WAVE SHIELDING MATERIAL, BUILDING MATERIAL WITH ELECTROMAGNETIC WAVE SHIELD, AND ARTICLE WITH ELECTROMAGNETIC WAVE SHIELDING MATERIAL

CROSS REFERENCE TO RELATED APPLICATIONS

The present application is a continuation of PCT/JP2018/003107 filed Jan. 31, 2018, which claims priority to Japanese Patent Application No. 2017-078294, filed Apr. 11, 2017, the entire contents of each of which are incorporated herein by reference.

TECHNICAL FIELD

The present disclosure relates to an electromagnetic wave shielding material shielding an electromagnetic wave having a specific frequency as well as a building material and an article (goods) including the electromagnetic wave shielding material.

BACKGROUND

A material described in Patent Document 1 (identified below) is conventionally known as an electromagnetic wave shielding material, for example. Specifically, Patent Document 1 discloses a shielding material on which a plurality of FSS (frequency selective surface) elements made up of thin line patterns are arranged for shielding (selectively blocking or transmitting) an electromagnetic wave having a specific frequency with the FSS elements.

Patent Document 1: Japanese Laid-Open Patent Publication No. 2007-180114.

However, for the electromagnetic wave shielding material of Patent Document 1, the FFS elements reflect electromagnetic waves, and the reflected electromagnetic waves may adversely affect another device. Additionally, if the electromagnetic wave shielding material of Patent Document 1 is attached to a wall, an electric length of the FSS elements serving as an antenna is changed due to the permittivity of the wall, which may result in deterioration in antenna characteristics. Therefore, the usage of the electromagnetic wave shielding material of Patent Document 1 is limited by environment.

SUMMARY OF THE INVENTION

In view of the above, an object of the present disclosure is to provide an electromagnetic wave shielding material capable of preventing usage environment from being limited as well as a building material and an article including the electromagnetic wave shielding material.

Accordingly, an electromagnetic wave shielding material according to the present disclosure is configured as an electromagnetic wave shielding material for shielding an electromagnetic wave having a specific frequency, comprising a substrate, and a plurality of resonance loops arranged on the substrate. Moreover, the plurality of resonance loops are arranged to be magnetically coupled to each other, and wherein each of the resonance loops is configured to form an LC parallel resonance circuit and resonate at the specific frequency.

According to another aspect of the disclosure, an electromagnetic wave shielding material is configured as a building material including an electromagnetic wave shielding material for shielding an electromagnetic wave having a specific frequency, the electromagnetic wave shielding material including a substrate, and a plurality of resonance loops arranged on the substrate. In this aspect, the plurality of resonance loops are arranged to be magnetically coupled to each other, and each of the resonance loops is configured to form an LC parallel resonance circuit and resonate at the specific frequency.

According to another aspect of the disclosure, an electromagnetic wave shielding material is configured as an article including an electromagnetic wave shielding material for shielding an electromagnetic wave having a specific frequency, the electromagnetic wave shielding material including a substrate, and a plurality of resonance loops arranged on the substrate. Moreover, the plurality of resonance loops are arranged to be magnetically coupled to each other, and wherein each of the resonance loops is configured to form an LC parallel resonance circuit and resonate at the specific frequency.

According to exemplary embodiments described in the present disclosure, the electromagnetic wave shielding material can be used in various environments, and is not limited, unlike previous solutions.

DETAILED DESCRIPTION

Figure 1:
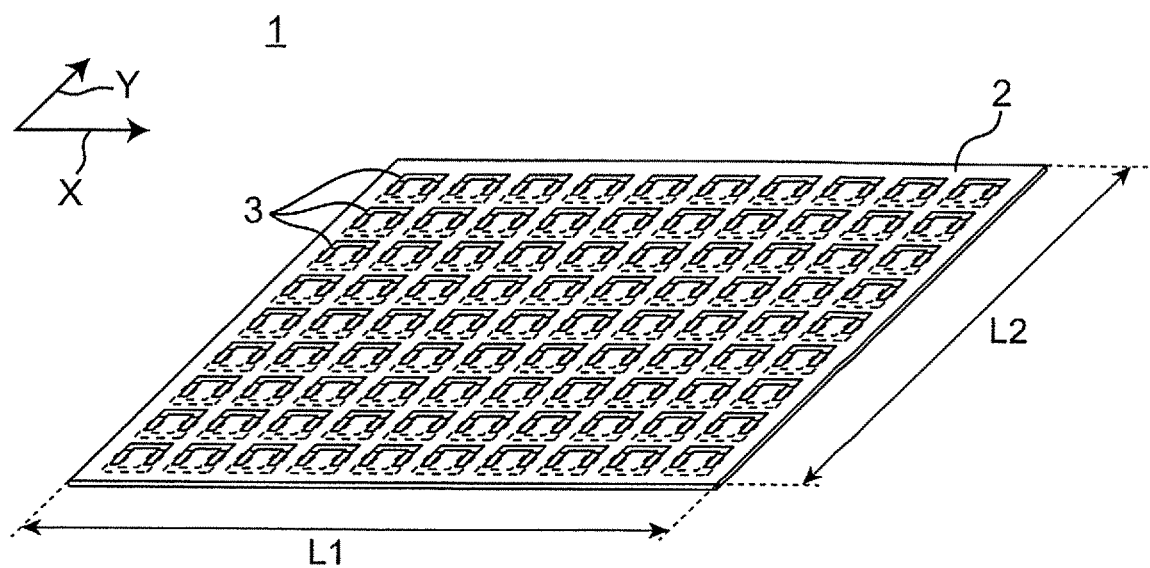
FIG. 1 is a perspective view of an electromagnetic wave shielding material according to an exemplary embodiment of the present disclosure.

According to an exemplary aspect of the present disclosure, an electromagnetic wave shielding material is provided that is configured to shield an electromagnetic wave having a specific frequency. In this embodiment, the electromagnetic wave shielding material comprises a substrate, and a plurality of resonance loops arranged on the substrate, wherein the plurality of resonance loops are arranged to be magnetically coupled to each other, and wherein each of the resonance loops is configured to form an LC parallel resonance circuit and resonate at the specific frequency. Moreover, the term "specific" can refer to a specified or predetermined/predefined or otherwise known frequency.

With this configuration, since each of the resonance loops forms an inductor-capacitor (LC) parallel resonance circuit, all the energy of the received electromagnetic wave having the specific frequency can be converted into a magnetic field, and the reflection of the electromagnetic waves can be suppressed. Additionally, this configuration reduces the influence of permittivity of a member to which the electromagnetic wave shielding material is attached. Moreover, since the plurality of resonance loops are arranged to be magnetically coupled to each other, any one of the resonance loops can convert the energy of the electromagnetic wave of the specific frequency into a magnetic field. This causes adjacent resonance loops to be magnetically coupled to each other in a linked manner. As a result, the energy of the electromagnetic wave having the specific frequency can be attenuated, and the reflection of the electromagnetic wave can be suppressed further. Therefore, the electromagnetic wave shielding material is not limited in usage by environment.

In one embodiment, the plurality of resonance loops are arranged such that a length in an arrangement direction of the plurality of resonance loops is ½ wavelength or more at the specific frequency. In this embodiment, the plurality of resonance loops are configured to restrain the electromagnetic wave of the specific frequency from passing (detouring) through a portion of the shield that does not contain the plurality of resonance loops, so that the resonance loops can more reliably receive the electromagnetic wave having the specific frequency. Consequently, a shielding effect can be improved in this exemplary aspect.

In one embodiment, each of the resonance loops is a minute loop having a perimeter less than ½ wavelength at the specific frequency. In this embodiment, the converted magnetic field can be restrained from radiating beyond a particular threshold, so that the usage environment of the electromagnetic wave shielding material can further be prevented from being limited.

According to an exemplary aspect, the substrate is made of a sheet member having flexibility. With this configuration, the electromagnetic wave shielding material can be attached to various shapes, improving the usability of the electromagnetic wave shielding material.

According to an exemplary aspect, each of the resonance loops includes a transparent electrode. With this configuration, for example, even when the electromagnetic wave shielding material is affixed to transparent glass, the presence of the resonance loops can be made inconspicuous, improving the usability of the electromagnetic wave shielding material.

According to an exemplary aspect, the substrate includes a first principal surface and a second principal surface opposing the first principal surface. Moreover, each of the resonance loops includes a first conductor formed on the first principal surface and a second conductor formed on the second principal surface. When viewed through the substrate in a direction orthogonal to the first principal surface or the second principal surface, the first conductor and the second conductor have respective portions overlapping each other to form a closed loop and are capacitively coupled via the substrate. With this configuration, a capacitor can be formed by using only the permittivity of the substrate between the first conductor and the second conductor, eliminating the need for separately including a capacitor part. As a result, the thickness and cost of the electromagnetic wave shielding material can be reduced. Additionally, the durability of the electromagnetic wave shielding material can be improved. Since the capacitors constituting a portion of the LC parallel resonance circuit are formed only between electrodes of the first conductor and the second conductor of the substrate, even when the electromagnetic wave shielding material is affixed to a dielectric material such as glass and a wall on the outside of a space between the electrodes, frequency change is small. This also improves the usage of the electromagnetic wave shielding material.

In an exemplary aspect, the substrate includes a first sheet member and a second sheet member laminated to each other, and the plurality of resonance loops are arranged on each of the first sheet member and the second sheet member. With this configuration, the shielding effect can further be improved.

In an exemplary aspect, the plurality of resonance loops have the same or substantially the same inner and outer diameter dimensions and is arranged at regular intervals, and the first sheet member and the second sheet member are arranged such that a plurality of resonance loops arranged on the first sheet member are shifted in a plane direction from a plurality of resonance loops arranged on the second sheet members. With this configuration, the shielding effect can further be improved.

In an exemplary aspect, the plurality of resonance loops include a first resonance loop group made up of at least two or more resonance loops resonating at a first frequency, and a second resonance loop group made up of at least two or more resonance loops resonating at a second frequency different from the first frequency. This configuration can shield both the electromagnetic waves of the first frequency and the electromagnetic waves of the second frequency, improving usability of the electromagnetic wave shielding material further.

In an exemplary aspect, the substrate includes a first sheet member and a second sheet member laminated to each other, the first resonance loop group is arranged on the first sheet member, and the second resonance loop group is arranged on the second sheet member. With this configuration, the first sheet member and the second sheet member can be configured as members shielding electromagnetic waves having different respective specific frequencies. This makes the design of the electromagnetic wave shielding material easier as compared to a configuration in which one sheet member shields electromagnetic waves having different specific frequencies. Additionally, this improves usability of the electromagnetic wave shielding material further.

In an exemplary aspect, the LC parallel resonance circuit has a Q value of 1 or more and 30 or less. This configuration can increase an amount of attenuation of the energy of the electromagnetic wave having a specific frequency when the adjacent resonance loops are magnetically coupled to each other in a linked manner, and the reflection of the electromagnetic waves can further be suppressed.

According to an aspect of the present disclosure, a building material with an electromagnetic wave shielding material is configured as a building material including an electromagnetic wave shielding material for shielding an electromagnetic wave having a specific frequency. The electromagnetic wave shielding material may include a substrate, and a plurality of resonance loops arranged on the substrate. The plurality of resonance loops may be arranged to be magnetically coupled to each other. Further, each of the resonance loops is configured to form an LC parallel resonance circuit and resonate at the specific frequency.

With this configuration, since each of the resonance loops are configured to form an LC parallel resonance circuit, all energy of the received electromagnetic wave having the specific frequency can be converted into a magnetic field, and the reflection and/or re-radiation of the electromagnetic waves can be suppressed. Additionally, this enables a reduction in influence of permittivity of the building material to which the electromagnetic wave shielding material is attached. Moreover, since the plurality of resonance loops are arranged to be magnetically coupled to each other, any of the resonance loops converts the energy of the electromagnetic wave having the specific frequency into a magnetic field so that the adjacent resonance loops can magnetically be coupled to each other in a linked manner. As a result, the energy of the electromagnetic wave having the specific frequency can be attenuated, and the reflection of the electromagnetic wave can further be suppressed, further improving usage environments for the electromagnetic wave shielding material.

According to an exemplary aspect of the present disclosure, an article with an electromagnetic wave shielding material is configured as including an electromagnetic wave shielding material for shielding an electromagnetic wave having a specific frequency. The electromagnetic wave shielding material can include a substrate, and a plurality of resonance loops arranged on the substrate. The plurality of resonance loops may be arranged to be magnetically coupled to each other, and each of the resonance loops is configured to form an LC parallel resonance circuit and resonate at the specific frequency.

With this configuration, since each of the resonance loops is configured to form an LC parallel resonance circuit, all the energy of the received electromagnetic wave having the specific frequency can be converted into a magnetic field, and the reflection and/or re-radiation of the electromagnetic waves can be suppressed. Additionally, this enables a reduction in influence of permittivity of the article to which the electromagnetic wave shielding material is attached. Moreover, since the plurality of resonance loops are arranged to be magnetically coupled to each other, any of the resonance loops converts the energy of the electromagnetic wave having the specific frequency into a magnetic field so that the adjacent resonance loops can magnetically be coupled to each other in a linked manner. Since the conductor constituting this resonance loop has a resistance component, the electromagnetic wave energy is converted into heat in each of the resonance loops. As a result, the energy of the electromagnetic wave having the specific frequency can be attenuated, and the reflection of the electromagnetic wave can further be suppressed.

An electromagnetic wave shielding material according to an embodiment will now be described with reference to the accompanying drawings. In the drawings, substantially the same members are denoted by the same reference numerals.

Exemplary Embodiment

FIG. 1 is a perspective view of an electromagnetic wave shielding material according to an embodiment of the present disclosure.

An electromagnetic wave shielding material 1 according to this embodiment shields electromagnetic waves of a specific frequency. Specifically, the electromagnetic wave shielding material 1 selectively blocks or transmits electromagnetic waves of a specific frequency.

As shown in FIG. 1, the electromagnetic wave shielding material 1 includes a substrate 2 and a plurality of resonance loops 3 arranged on the substrate 2.

The substrate 2 is made of a sheet member having flexibility. The substrate 2 is, for example, a PET (polyethylene terephthalate) film, a PEN (polyethylene naphthalate) film, a polyimide film, paper, or a laminated body thereof and is configured to include an insulator layer. The substrate 2 has heat resistance in some exemplary aspects.

The plurality of the resonance loops 3 are arranged such that the resonance loops are magnetically coupled to each other. The plurality of the resonance loops 3 are loop-shaped conductors having the same or substantially the same inner and outer diameters and is arranged at regular intervals. In this embodiment, the plurality of the resonance loops 3 are arranged in a matrix shape in a lateral direction X and a longitudinal direction Y on the substrate 2. The plurality of the resonance loops 3 are arranged such that lengths L1, L2 in arrangement directions of the plurality of the resonance loops 3, i.e., the lateral direction X and the longitudinal direction Y, are ½ wavelength or more at a specific frequency, according to some aspects.

Figure 2A:
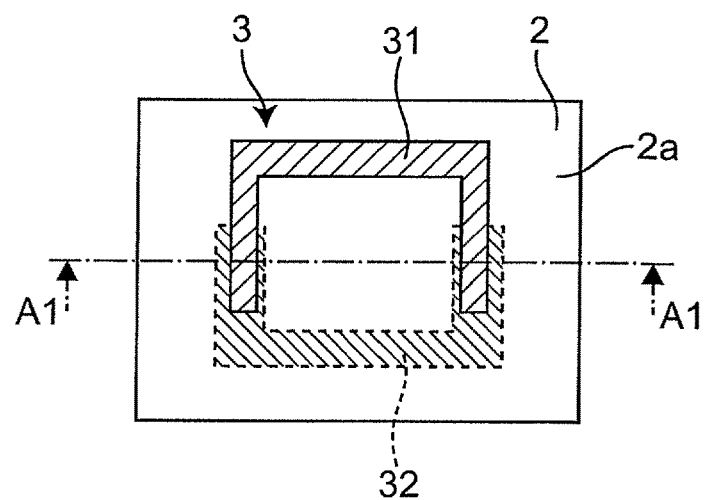
FIG. 2A is a plan view of a resonance loop of the electromagnetic wave shielding material shown in FIG. 1.
Figure 2B:
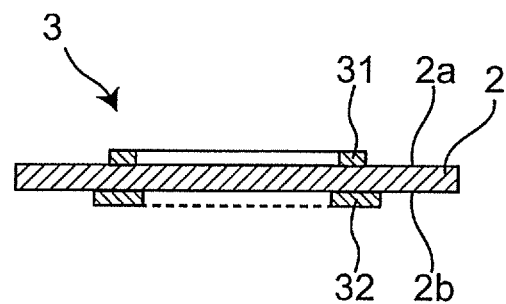
FIG. 2B is a cross-sectional view taken along axis A1-A1 of FIG. 2A.

FIG. 2A is a plan view of the resonance loop 3. FIG. 2B is a cross-sectional view taken along a line A1-A1 of FIG. 2A.

As shown in FIGS. 2A and 2B, the resonance loop 3 includes a U-shaped first conductor 31 formed on a first principal surface 2a of the substrate 2 and a U-shaped second conductor 32 formed on a second principal surface 2b opposite to the first principal surface 2b. When viewed through the substrate 2 in a direction orthogonal to the first principal surface 2a (or the second principal surface 2b), the first conductor 31 and the second conductor 32 are arranged, in some aspects, to have end portions of respective conductor patterns overlapping each other to form a closed loop and are capacitively coupled via the substrate 2.

Figure 3:
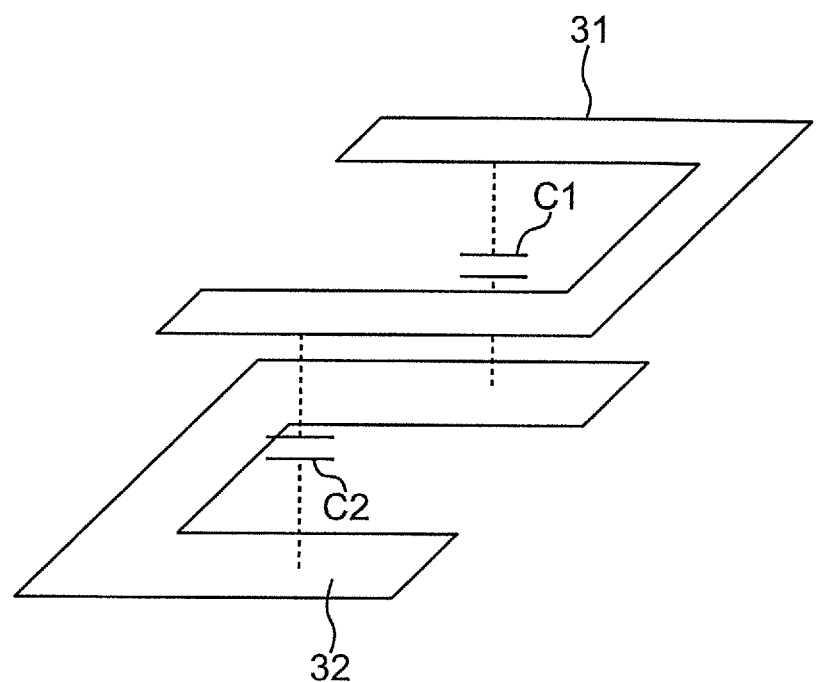
FIG. 3 is a perspective view showing an image in which capacitors serving as capacitance components are formed between two loop electrodes constituting the resonance loop of FIG. 2A.
Figure 4:
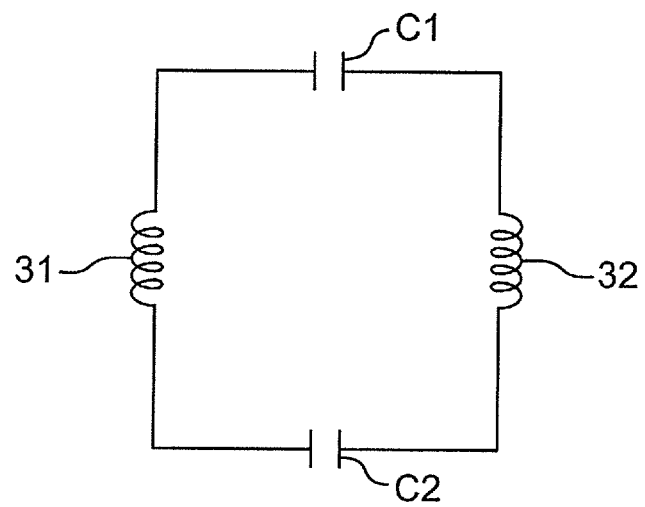
FIG. 4 is a circuit diagram of the configuration illustrated in FIG. 3.

FIG. 3 is a perspective view showing an image in which capacitors C1, C2 serving as capacitance components are formed between the first conductor 31 and the second conductor 32, according to exemplary aspects of the present disclosure. FIG. 4 is an equivalent circuit diagram of FIG. 3.

As shown in FIG. 3, the capacitors C1, C2 are formed between the first conductor 31 and the second conductor 32 by the permittivity of the substrate 2 and an overlapping area. As shown in FIG. 4, the resonance loop 3 has an LC parallel resonance circuit formed by the capacitors C1, C2, an inductance component of the first conductor 31, and an inductance component of the second conductor 32.

The resonance loop 3 is configured to resonate at a specific frequency. For example, the sizes (outer shapes, line widths, etc.) of the first conductor 31 and the second conductor 32 and the capacitances of the capacitors C1, C2 are set such that the resonance loop 3 has a resonance frequency in the UHF band (860 MHz to 960 MHz). For example, the capacitances of the capacitors C1, C2 are adjusted depending on an amount of overlap between the first conductor 31 and the second conductor 32 when viewed through the substrate 2 in a direction orthogonal to the first principal surface 2a. The capacitances of the capacitors C1, C2 can also be adjusted by a material of the substrate 2, for example.

The resonance loop 3 is a minute loop having a perimeter less than ½ wavelength at the specific frequency. For example, if the specific frequency is 900 MHz, the outer diameter dimension of the resonance loop 3 is 7 mm×7 mm, for example. An area of an inner circumferential portion of the resonance loop 3 is 30 mm$^2$ or more and 900 mm$^2$ or less, for example. The resonance loop 3 is made of an electrode material such as aluminum, copper, and silver, or zinc oxide, for example. The resonance loop 3 can be formed by photolithography or etching after forming aluminum, etc., on an entire surface of a PET film used as the substrate 2, for example. The resonance loop 3 can also be formed by printing on paper used as the substrate 2, for example.

Figure 5:
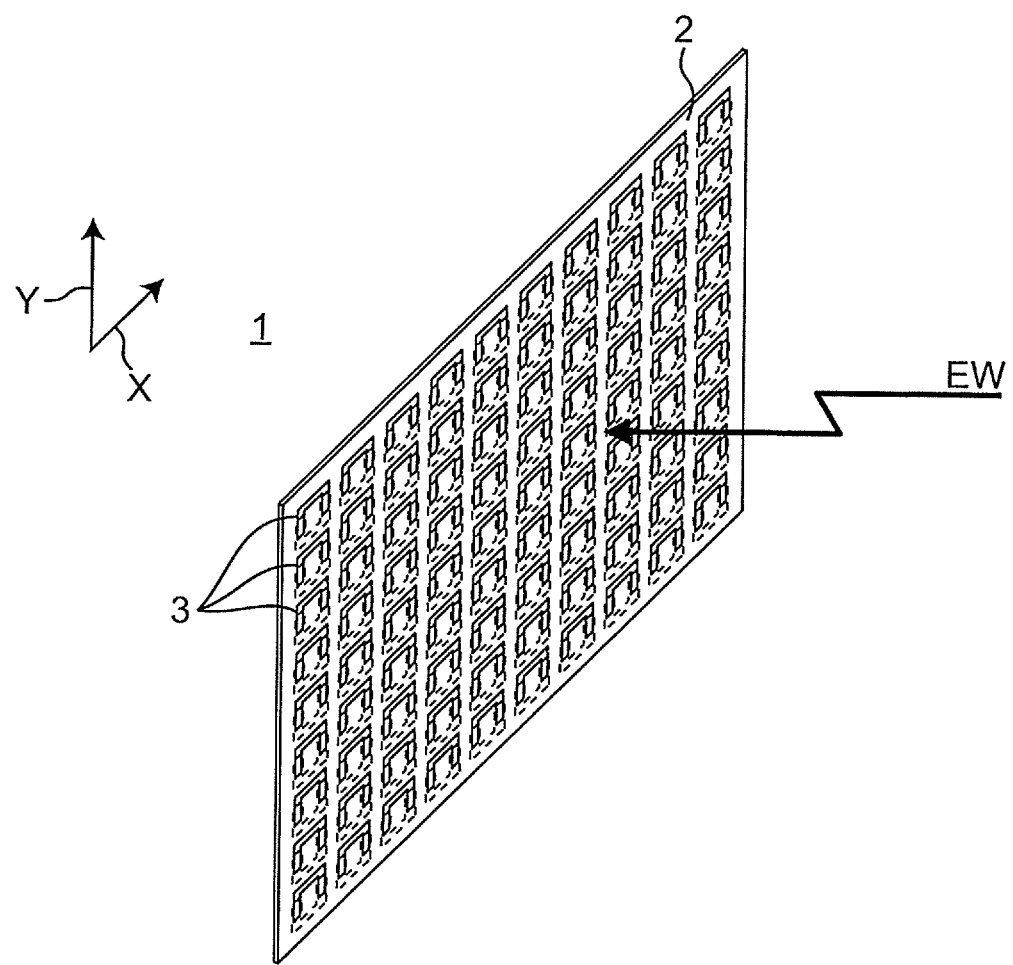
FIG. 5 is a perspective view of an electromagnetic wave incident on the electromagnetic wave shielding material of FIG. 1.
Figure 6:
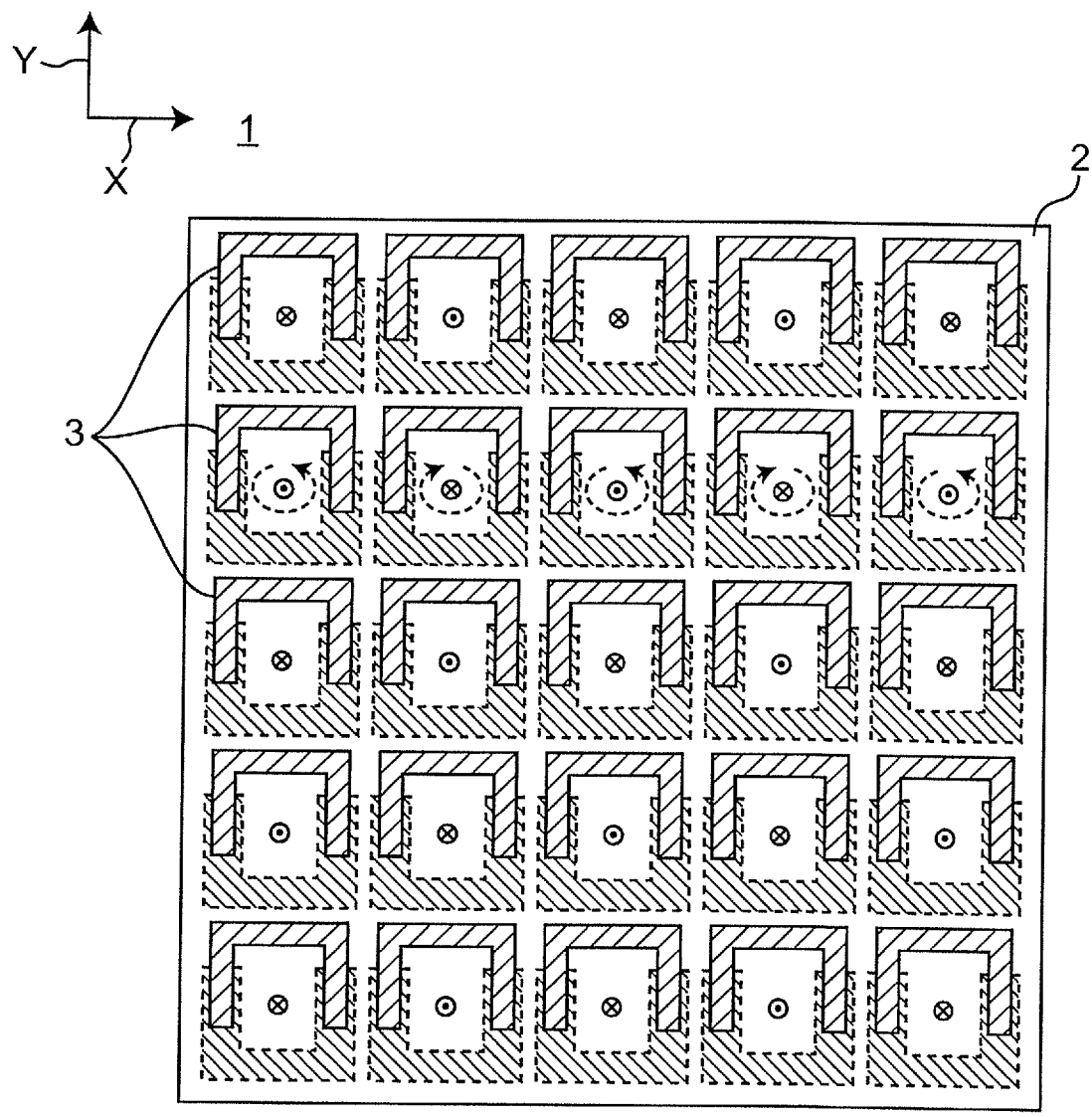
FIG. 6 is a plan view of the electromagnetic wave shielding material of FIG. 1, showing how currents are excited in a plurality of resonance loops.
Figure 7:
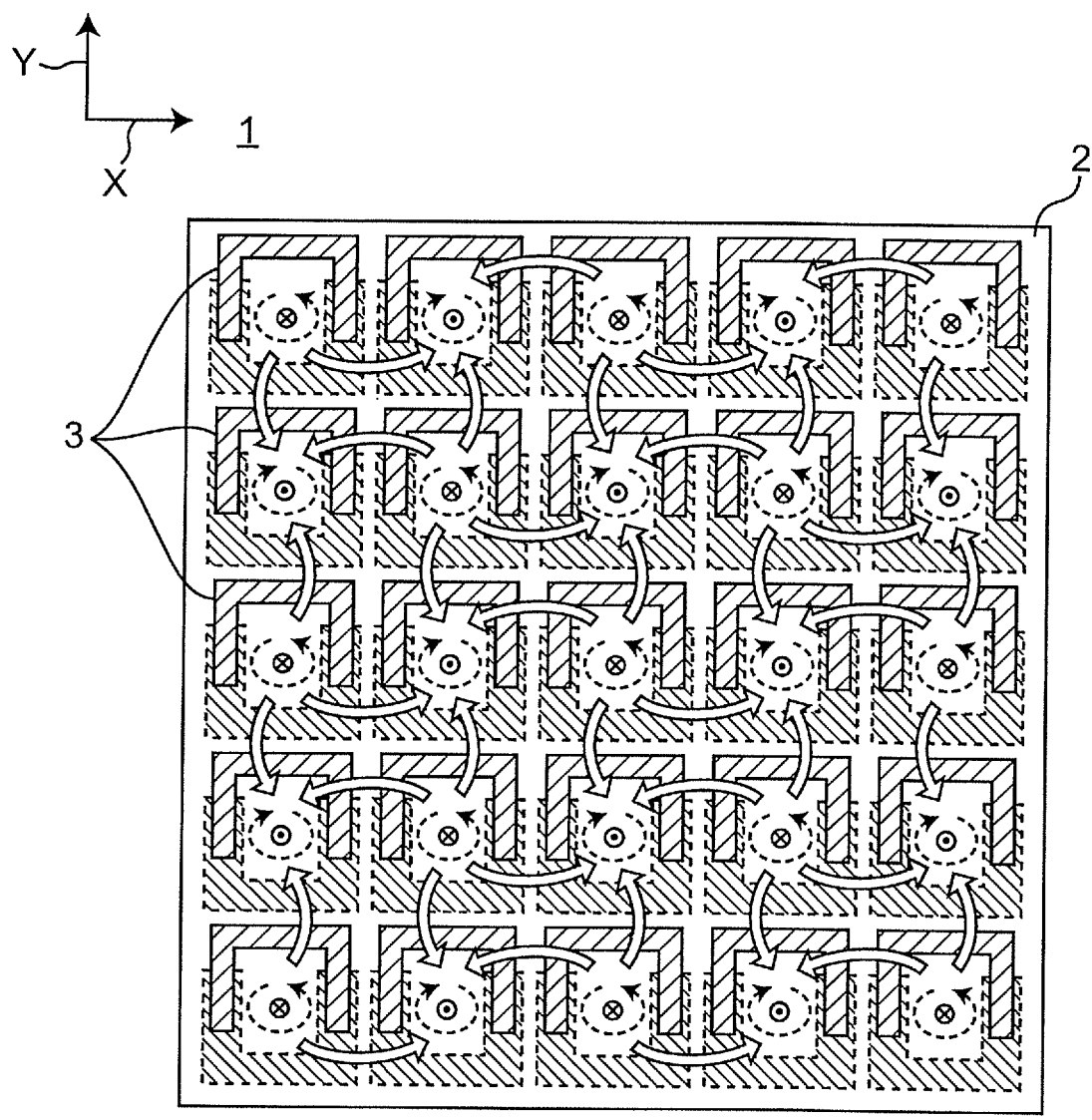
FIG. 7 is a plan view of the electromagnetic wave shielding material of FIG. 1, showing how the plurality of resonance loops are magnetically coupled to each other.
Figure 8:
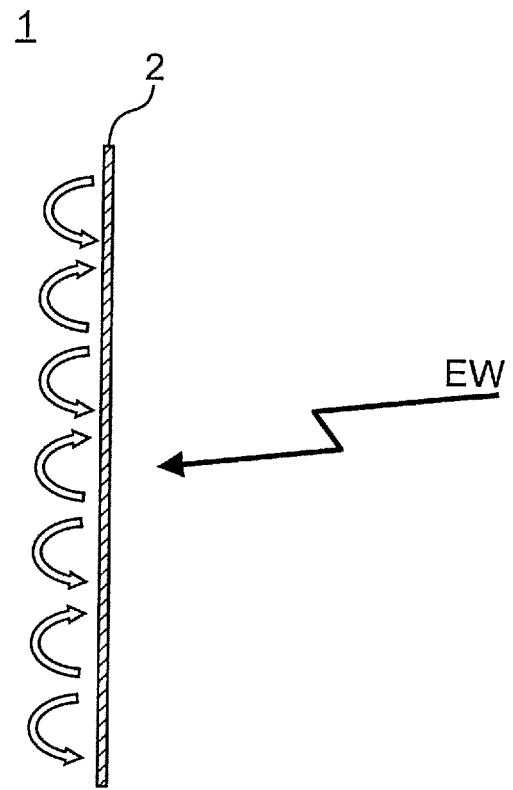
FIG. 8 is a side view of the electromagnetic wave shielding material of FIG. 1, showing how the electromagnetic wave incident on the electromagnetic wave shielding material of FIG. 1 is converted into a magnetic field.

A shielding operation of the electromagnetic wave shielding material 1 will be described. FIG. 5 is a perspective view showing an electromagnetic wave (EW) incident on the electromagnetic wave shielding material 1. FIGS. 6 and 7 are plan views of the electromagnetic wave shielding material 1. FIG. 8 is a side view showing how the electromagnetic wave EW incident on the electromagnetic wave shielding material 1 is converted into a magnetic field. In FIG. 6, dashed arrows indicate current flow directions. In FIG. 7, dashed arrows indicate current flow directions, and white arrows indicate magnetic-field flow directions. In FIG. 8, white arrows indicate magnetic-field flow directions. In FIGS. 6 and 7, for convenience of description, it is assumed that the five resonance loops 3 are arranged on each of the lateral and longitudinal directions X, Y in a matrix shape.

First, as shown in FIG. 5, the electromagnetic wave EW is incident on the electromagnetic wave shielding material 1. The electromagnetic wave EW is, for example, a signal of a circularly-polarized wave. The resonance loops 3 constituting the electromagnetic wave shielding material 1 receive the electromagnetic wave EW having a specific frequency (e.g., 900 MHz), thereby resulting in parallel resonance. As a result, a current is excited in at least one of the resonance loops 3 as indicated by the dashed arrows shown in FIG. 6.

A magnetic field is generated by the current excited in the resonance loop 3, and a current is excited in the resonance loop 3 adjacent to the resonance loop, so that a magnetic field is generated. Therefore, the energy of the electromagnetic wave EW is converted into the magnetic field. In this way, as indicated by the white arrows of FIGS. 7 and 8, the adjacent resonance loops 3 are magnetically coupled to each other in a linked manner. In this process, the energy of the electromagnetic wave EW having the specific frequency is attenuated by resistance components of the conductors of the resonance loops, and therefore, reflection and re-radiation of the electromagnetic wave EW are suppressed.

According to this embodiment, since each of the resonance loops 3 form an LC parallel resonance circuit, all the energy of the received electromagnetic wave EW having the specific frequency can be converted into a magnetic field and the reflection of the electromagnetic wave EW can be suppressed. Additionally, the resonance loop is configured to form a closed loop circuit enabling a reduction in influence of permittivity of a member to which the electromagnetic wave shielding material 1 is attached. Moreover, since the plurality of the resonance loops 3 are arranged to be magnetically coupled to each other, any of the resonance loops 3 may convert the energy of the electromagnetic wave EW having the specific frequency into a magnetic field so that the adjacent resonance loops 3 can magnetically be coupled to each other in a linked manner. As a result, the energy of the electromagnetic wave EW having the specific frequency can be attenuated, and the reflection of the electromagnetic wave EW can further be suppressed, improving the usage environment of the electromagnetic wave shielding material 1.

According to this embodiment, since the plurality of the electrically-closed resonance loops 3 are arranged like floating islands, the reflection of the electromagnetic wave EW can be suppressed without grounding the electromagnetic wave shielding material 1.

According to this embodiment, the plurality of the resonance loops 3 are arranged such that lengths L1, L2 in the arrangement directions of the plurality of the resonance loops 3, i.e., the lateral direction X and the longitudinal direction Y, are ½ wavelength or more at the specific frequency. This can restrain the electromagnetic wave EW having the specific frequency from passing (detouring) through a portion without the plurality of the resonance loops 3, so that the resonance loops 3 can more reliably receive the electromagnetic wave EW having the specific frequency. Consequently, the shielding effect can be improved.

According to this embodiment, each of the resonance loop 3 is configured to have a perimeter less than ½ wavelength at the specific frequency. Therefore, the converted magnetic field can be restrained from excessively radiating, improving the usage environment of the electromagnetic wave shielding material 1.

According to this embodiment, the substrate 2 is made of a sheet member having flexibility. As a result, the electromagnetic wave shielding material 1 can be attached to various shapes, improving usability of the electromagnetic wave shielding material.

According to this embodiment, each of the resonance loops 3 includes the first conductor 31 formed on the first principal surface 2a of the substrate 2 and the second conductor 32 formed on the second principal surface 2b of the substrate 2. When viewed through the substrate 2 in a direction orthogonal to the first principal surface 2a or the second principal surface 2b, the first conductor 31 and the second conductor 32 have respective portions overlapping each other to form a closed loop. The first conductor 31 and the second conductor 32 are configured to be capacitively coupled via the substrate 2. With this configuration, a capacitor can be formed by using the permittivity of the substrate 2, eliminating the need to separately include a capacitor part. As a result, the thickness and cost of the electromagnetic wave shielding material 1 can be reduced. Additionally, the durability of the electromagnetic wave shielding material 1 can be improved. The capacitors C1, C2 constituting a portion of the LC parallel resonance circuit are formed only by the overlapping area of the electrode patterns and the permittivity of the substrate 2, and the capacitance value between the overlapping areas does not change even when the electromagnetic wave shielding material 1 is affixed to a dielectric material such as glass and a wall. In this configuration, a frequency change of the resonance frequency is minimized, improving the usage environment of the electromagnetic wave shielding material 1.

Those of ordinary skill in the art will recognize that the present disclosure is not limited to the embodiments described above, and can be implemented in various other forms. For example, in the above description, the plurality of the resonance loops 3 are arranged such that the lengths L1, L2 in the lateral direction X and the longitudinal direction Y are ½ wavelength or more at a specific frequency, however, the present disclosure is not limited thereto. For example, the plurality of the resonance loops 3 may be arranged such that the lengths L1, L2 in the lateral direction X and the longitudinal direction Y are less than ½ wavelength (e.g., a length corresponding to 3×3 resonance loops) at a specific frequency. Even with this configuration, the shielding effect can be obtained in the portion provided with the resonance loops 3. In this case, for example, a metal plate may be disposed to surround the periphery of the plurality of the resonance loops 3. With this configuration, the metal plate can restrain the electromagnetic wave EW having a specific frequency from passing (detouring) through a portion without the plurality of the resonance loops 3.

In the above description, the resonance loops 3 are made of aluminum, copper, or zinc oxide, however, the present disclosure is not limited thereto. For example, the resonance loops 3 may be made up of transparent electrodes of ITO (indium tin oxide). With this configuration, for example, even when the electromagnetic wave shielding material 1 is affixed to transparent glass, the presence of the resonance loops 3 can be made inconspicuous, improving usability of the electromagnetic wave shielding material 1.

Figure 9A:
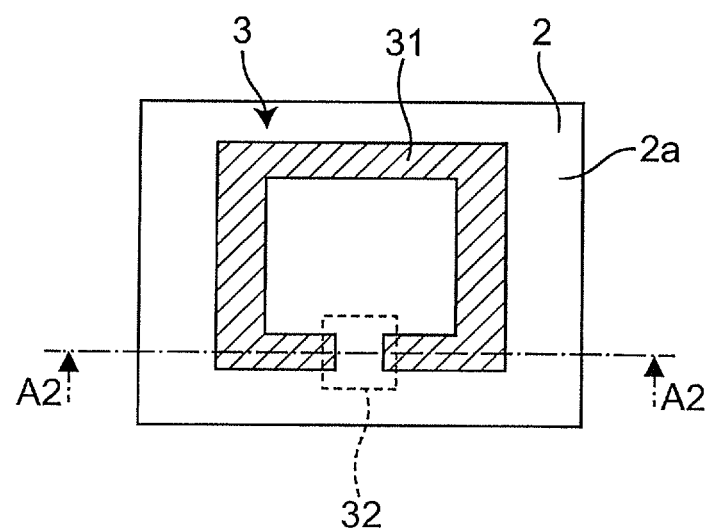
FIG. 9A is a plan view showing a modification of the resonance loop, according to exemplary embodiments of the present disclosure.
Figure 9B:
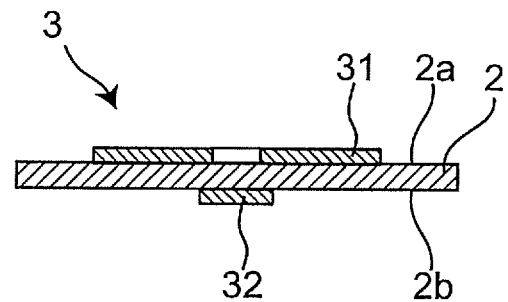
FIG. 9B is a cross-sectional view taken along axis A2-A2 of FIG. 9A.

In the above description, the first conductor 31 and the second conductor 32 are formed into a U-shape, and the resonance loop 3 is formed by overlapping the portions of the first conductor 31 and the second conductor 32 with each other such that a closed loop is formed, however, the present disclosure is not limited thereto. For example, as shown in FIGS. 9A and 9B, the first conductor 31 may be formed as an annular conductor having a partially opened shape, the second conductor 32 may be formed to cover the opening, and the resonance loop 3 may be formed by overlapping the portions of the first conductor 31 and the second conductor 32 with each other such that a closed loop is formed.

Figure 10A:
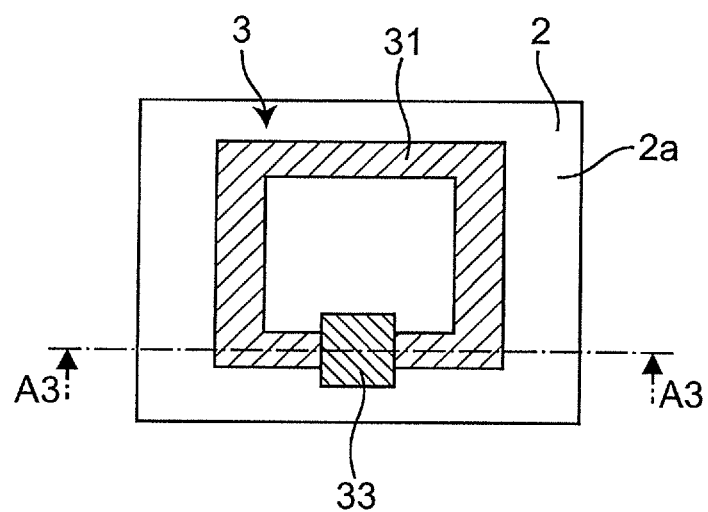
FIG. 10A is a plan view showing a modification of the resonance loop, according to another exemplary embodiment of the present disclosure.
Figure 10B:
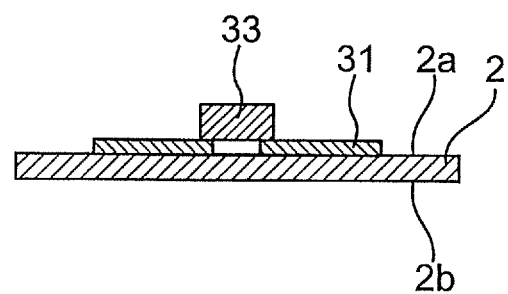
FIG. 10B is a cross-sectional view taken along axis A3-A3 of FIG. 10A.

In the above description, the resonance loop 3 includes the first conductor 31 formed on the first principal surface 2a of the substrate 2 and the second conductor 32 formed on the second principal surface 2b, however, the present disclosure is not limited thereto. For example, as shown in FIGS. 10A and 10B, the resonance loop 3 may be configured to include the first conductor 31 that is a partially opened annular conductor and a capacitor element 33 connected to both end portions of the first conductor 31 on the first principal surface 2a of the substrate 2. Alternatively, for example, the first conductor 31 may be formed on the first principal surface 2a of the substrate 2, a dielectric material may be applied as an insulating material on the first conductor 31, and the second conductor 32 may further be formed on the dielectric material to form the resonance loop 3.

In the drawings, the shape of the resonance loop 3 is shown as being rectangular or substantially rectangular, however, the present disclosure is not limited thereto. For example, the resonance loop 3 may be octagonal or may have other polygonal or circular shapes.

Figure 11:
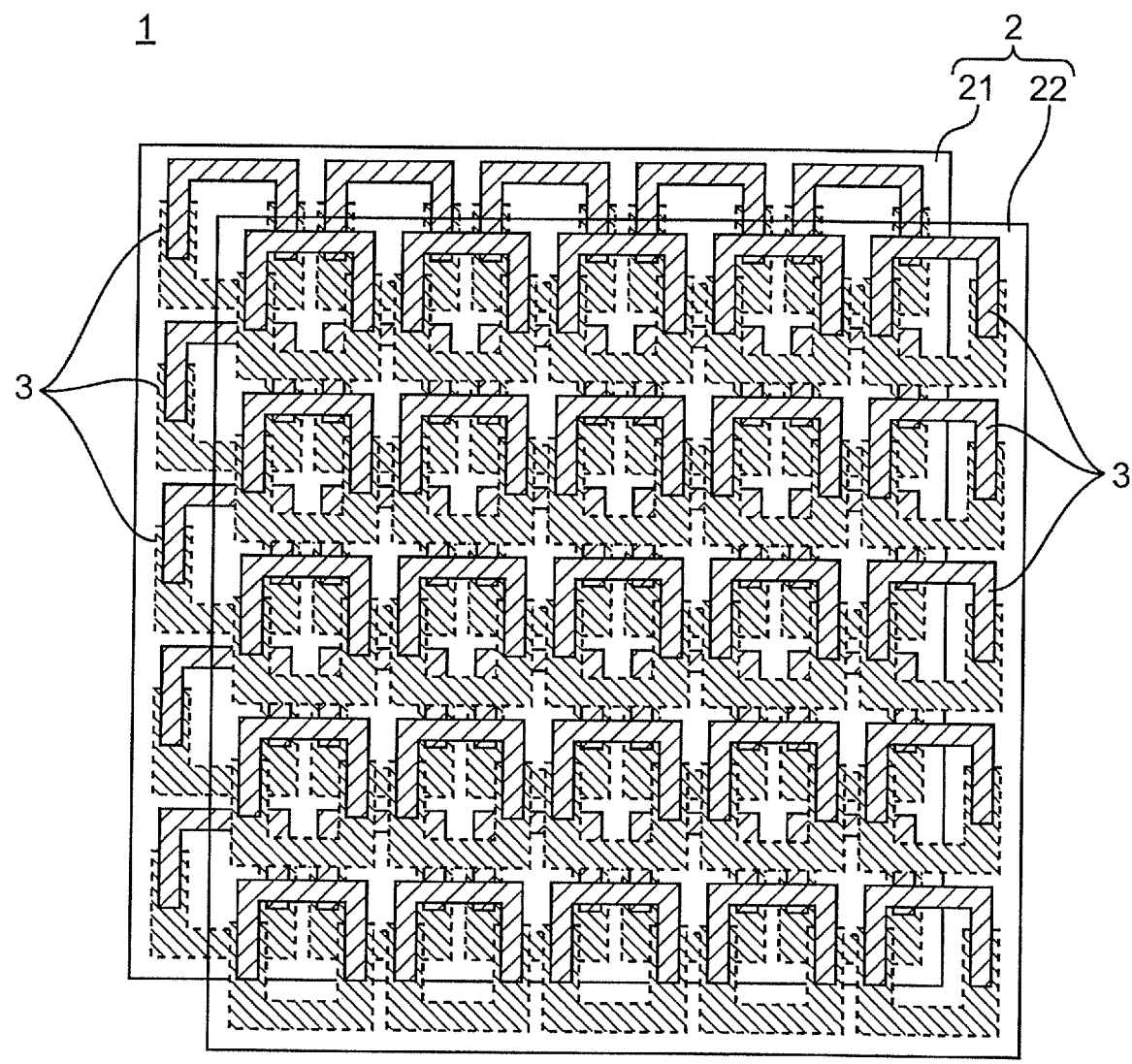
FIG. 11 is a plan view showing a modification of the electromagnetic wave shielding material of FIG. 1, according to another exemplary embodiment of the present disclosure.

In the above description, the substrate 2 is made up of one sheet member, and the plurality of the resonance loops are arranged on the sheet member, however, the present disclosure is not limited thereto. For example, the electromagnetic wave shielding material 1 may be formed by laminating two or more multiple sheet members having a plurality of the resonance loops 3 formed thereon. For example, as shown in FIG. 11, the substrate 2 may include a first sheet member 21 and a second sheet member 22, and a plurality of the resonance loops 3 may be arranged on each of the first sheet member 21 and the second sheet member 22. With this configuration, the shielding effect can further be improved, and the usage environment of the electromagnetic wave shielding material 1 can further be prevented from being limited.

In this case, in one aspect, the plurality of the resonance loops 3 have the same or substantially the same inner and outer diameter dimensions and is arranged at regular intervals and disposed such that a plurality of the resonance loops 3 arranged on the first sheet member 21 are shifted in a plane direction from a plurality of the resonance loops 3 arranged on the second sheet members 22. With this configuration, the shielding effect can further be improved, and the usage environment of the electromagnetic wave shielding material 1 can further be prevented from being limited.

Even if the electromagnetic wave shielding material 1 is formed by laminating two or more multiple sheet members having a plurality of the resonance loops 3 formed thereon, an LC parallel resonance circuit is configured for each of the sheet members, and therefore, the capacitance value is hardly affected by other members.

The plurality of the resonance loops 3 may include a plurality of resonance loop groups each made up of at least two or more of the resonance loops 3 and may be configured to resonate at a different specific frequency for each of the resonance loop groups. Specifically, the plurality of the resonance loops 3 may include a first resonance loop group made up of the at least two or more resonance loops 3 resonating at a first frequency and a second resonance loop group made up of the at least two or more resonance loops 3 resonating at a second frequency. This configuration can shield both the electromagnetic waves of the first frequency and the electromagnetic waves of the second frequency, improving the usability of the electromagnetic wave shielding material.

The first resonance loop group may be arranged on the first sheet member 21, and the second resonance loop group may be arranged on the second sheet member 22. In other words, the plurality of the resonance loops 3 (first resonance loop group) arranged on the first sheet member 21 may resonate at a frequency different from that of the plurality of the resonance loops 3 (second resonance loop group) arranged on the second sheet member 22. With this configuration, the first sheet member 21 and the second sheet member 22 can be configured as members shielding electromagnetic waves having different respective specific frequencies. This simplifies the design of the electromagnetic wave shielding material 1, as compared to a configuration in which one sheet member shields electromagnetic waves having different specific frequencies. Additionally, for example, a plurality of sheet members can be prepared in advance such that resonance loop groups having different resonance frequencies are arranged thereon, and the electromagnetic wave shielding material 1 can be formed by a combination of the sheet members changed depending on a demand. As a result, the electromagnetic wave shielding material can further be improved in usability.

Figure 12:
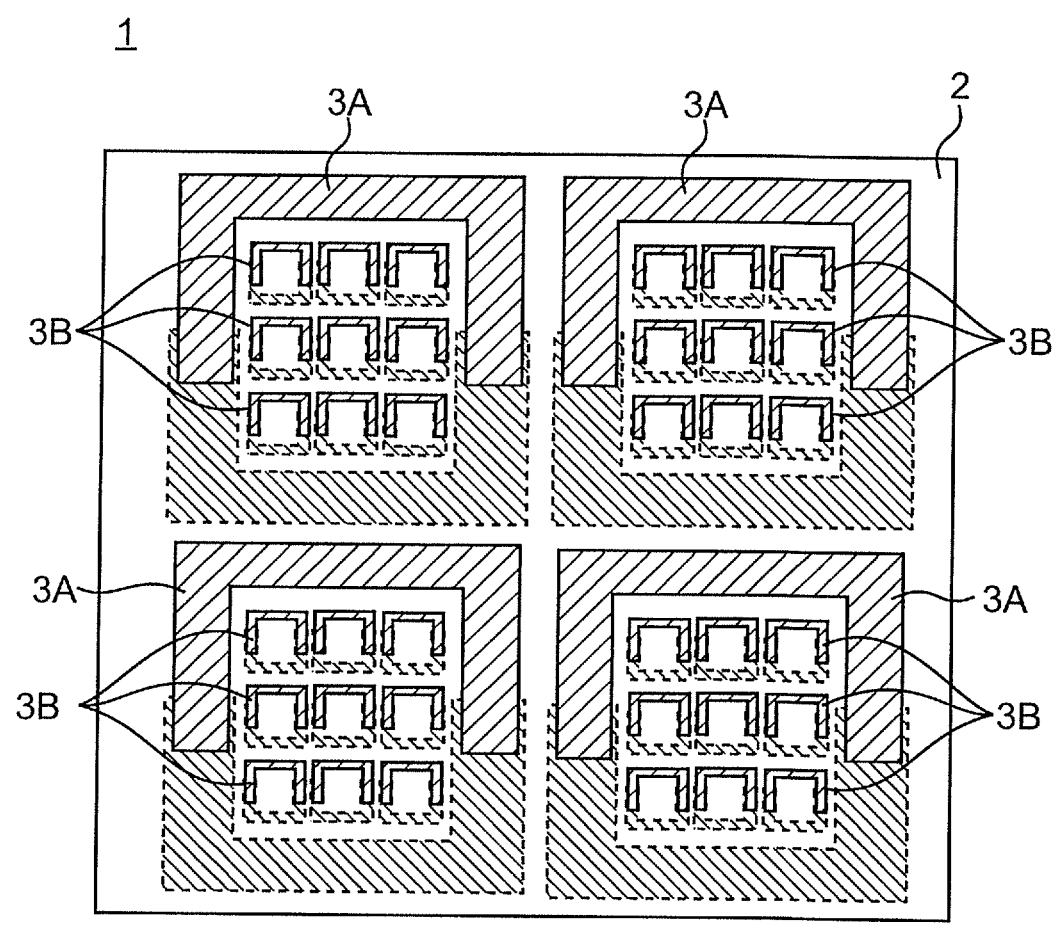
FIG. 12 is a plan view showing a modification of the electromagnetic wave shielding material of FIG. 1, according to another exemplary embodiment of the present disclosure.

In the above description, the resonance loops 3 have the same or substantially the same inner and outer diameter dimensions, however, the present disclosure is not limited thereto. The inner and outer diameter dimensions of the resonance loops 3 may be different. For example, as shown in FIG. 12, a plurality of small-diameter resonance loops 3B may be arranged inside each of a plurality of large-diameter resonance loops 3A. In this case, the resonance frequency may be different between the large-diameter resonance loops 3A and the small-diameter resonance loops 3B. As a result, the large-diameter resonance loops 3A and the small-diameter resonance loops 3B can be arranged on one sheet member, and the shield electromagnetic waves may be shielded at two frequencies.

In the above description, the plurality of the resonance loops 3 are exposed to the outside, however, the present disclosure is not limited thereto. A protective layer may be disposed to cover the plurality of the resonance loops 3.

The LC parallel resonant circuit formed by the resonance loop 3 preferably has a low Q value so that the energy of the electromagnetic waves having a specific frequency can be attenuated in an increased amount. On the other hand, when the Q value is too low, a current no longer flows through the LC parallel resonance circuit. Therefore, the Q value is preferably 1 or more and 30 or less. To make the Q value lower, for example, the resonance loop 3 may be made of a porous metal material. Additionally, for the material of the resonance loop 3, a metal material having a relatively large resistance value such as those containing a certain amount of an insulating material as impurities of may be used instead of pure metal. For example, a silver paste may be applied to the principal surface of the substrate 2, a dielectric paste serving as an insulating material may be applied onto the silver paste, and a silver paste may be applied onto the dielectric paste to form the first conductor 31 and the second conductor 32 of the resonance loops 3. This can increase an amount of attenuation of the energy of the electromagnetic wave having a specific frequency, and the reflection of the electromagnetic waves can further be suppressed.

(Building Material with Electromagnetic Wave Shielding Material)

A building material including the electromagnetic wave shielding material 1 (a building material with an electromagnetic wave shielding material) will hereinafter be described. In this description, the building material refers to a member used for a structure and finishing of a building. Examples of the building material include windows, walls, ceilings, floors, roofs, fittings, and wallpaper.

Figure 13:
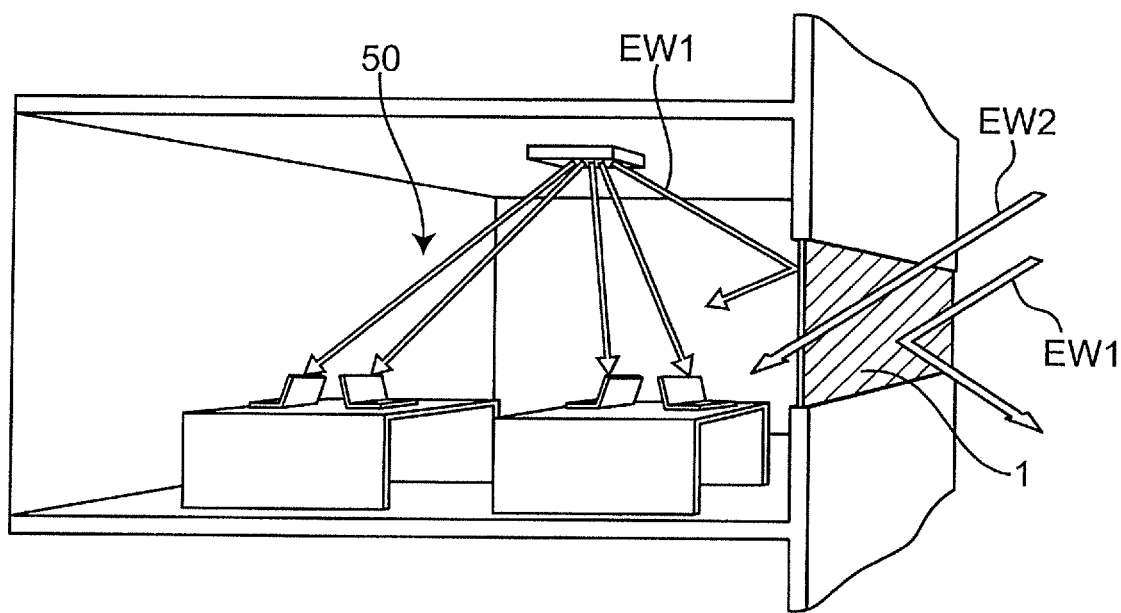
FIG. 13 is a perspective view showing an example in which an office window includes the electromagnetic wave shielding material.

FIG. 13 is a perspective view showing an example in which an exemplary building material, i.e., an office window, includes the electromagnetic wave shielding material 1. For example, in an office in which a wireless LAN 50 is used, radio waves EW1 having a frequency (e.g., 2.4 GHz, 5 GHz) used for the wireless LAN 50 may be intercepted. On the other hand, it may be desired to allow radio waves EW2 having a frequency (e.g., 900 MHz) used by mobile phones to enter inside the building.

In such a case, as shown in FIG. 13, the office window is configured to include the electromagnetic wave shielding material 1 configured to shield the radio waves EW1 having the frequency used for the wireless LAN 50. As a result, the electromagnetic wave shielding material 1 can shield the radio waves EW1 having the frequency used for the wireless LAN 50 so as not to leak the radio waves outside of the office. Additionally, the radio waves EW1 having the frequency used for the wireless LAN 50 can be prevented from entering inside the office from the outside causing radio wave interference. On the other hand, the radio waves EW2 having the frequency used by mobile phones can be allowed to enter the office.

Figure 14:
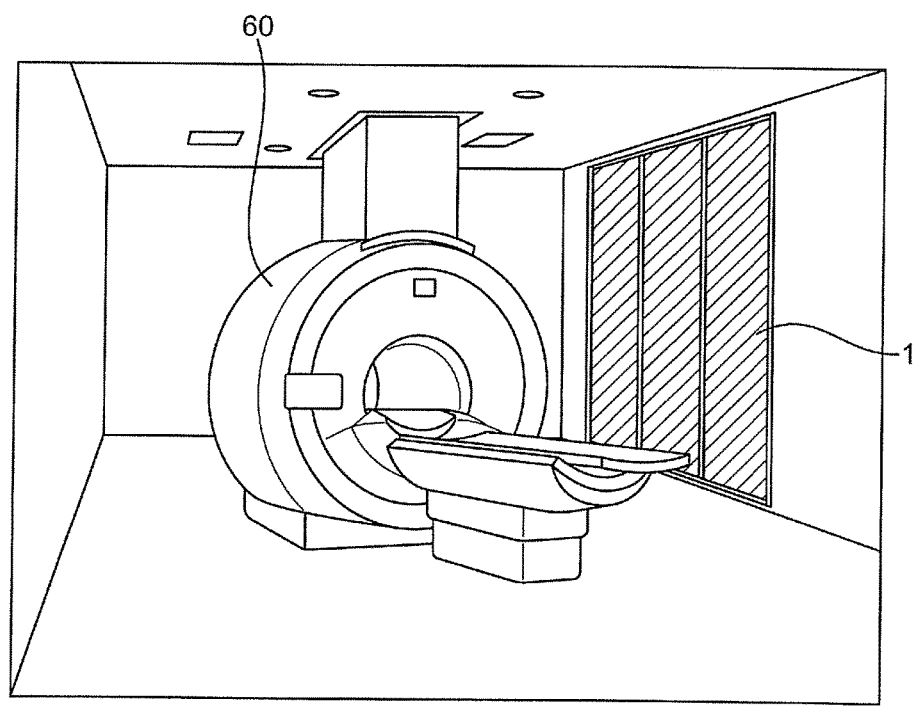
FIG. 14 is a perspective view showing an example in which a window of a room provided with an magnetic resonance imaging (MRI) apparatus includes the electromagnetic wave shielding material.

FIG. 14 is a perspective view showing an example in which an exemplary building material, i.e., a window of a room provided with an MRI (Magnetic Resonance Imaging) apparatus 60, include the electromagnetic wave shielding material 1. The MRI apparatus 60 may malfunction due to a specific frequency and may not be able to take an accurate MRI image without such shielding.

In such a case, as shown in FIG. 14, the window of the room is configured to include the electromagnetic wave shielding material 1 configured to shield radio waves having a frequency that may cause a malfunction of the MRI apparatus 60. As a result, the electromagnetic wave shielding material 1 can shield the radio waves having a frequency causing a malfunction of the MRI apparatus 60 so as to prevent the radio waves from entering inside the room.

Figure 15:
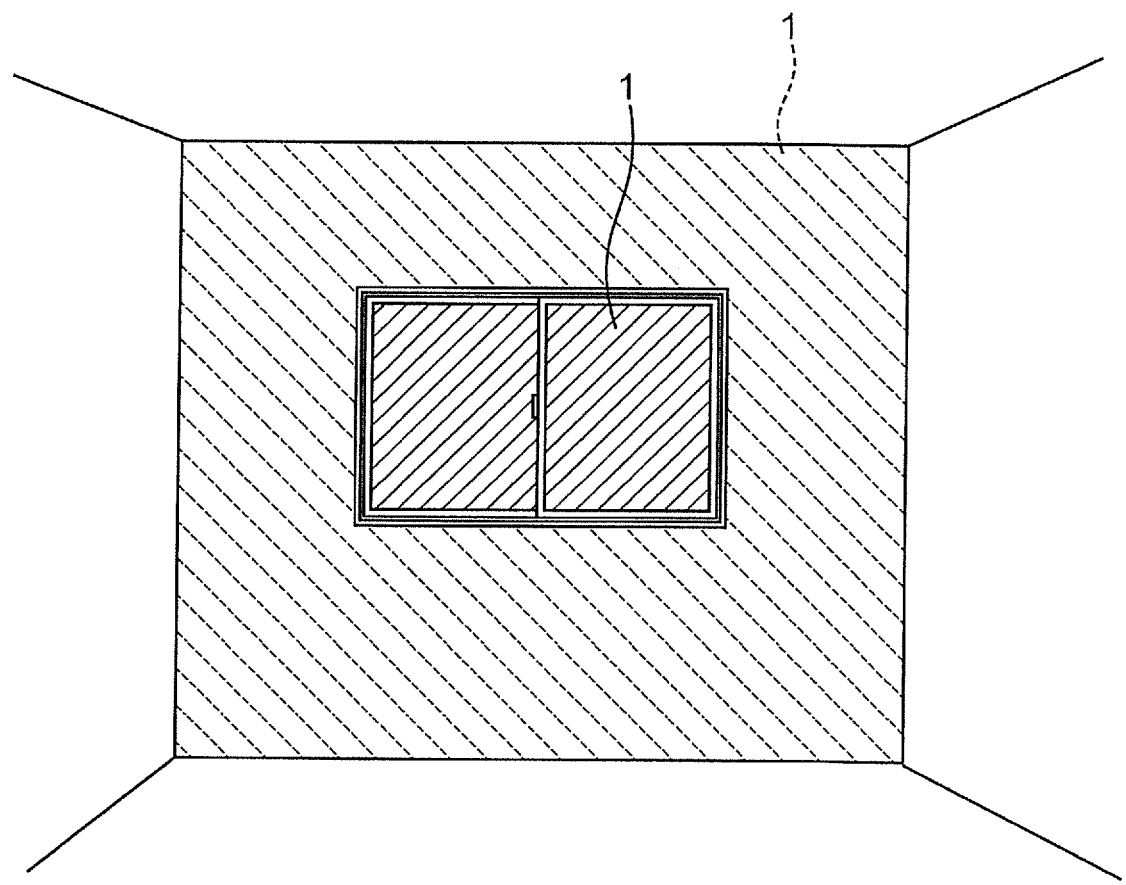
FIG. 15 is a perspective view showing an example in which a wall and a window of a house include the electromagnetic wave shielding material.

FIG. 15 is a perspective view showing examples of the building material, for example, a wall and a window of a house, that include the electromagnetic wave shielding material 1. For example, in a house, it is desired to prevent radio waves having a frequency (e.g., 2.4 GHz, 5 GHz) used for WiFi from leaking outside the building in some cases. On the other hand, it may be desired to allow radio waves having frequencies used for television (e.g., terrestrial: 470 MHz to 770 MHz, BS: 11 GHz to 12.5 GHz, analog: 90 MHz to 770 MHz) to enter inside the building.

In such a case, as shown in FIG. 15, the walls and the windows of the house are configured to include the electromagnetic wave shielding material 1 configured to shield the radio waves having the frequency used for WiFi. As a result, the electromagnetic wave shielding material 1 can shield the radio waves having the frequency used for WiFi so as not to leak the radio waves to the outside of the house. Additionally, the radio waves having the frequency used for WiFi can be prevented from entering inside the house from the outside and causing radio wave interference. On the other hand, the radio waves having the frequencies used for television can be allowed to enter inside the house.

Figure 16:
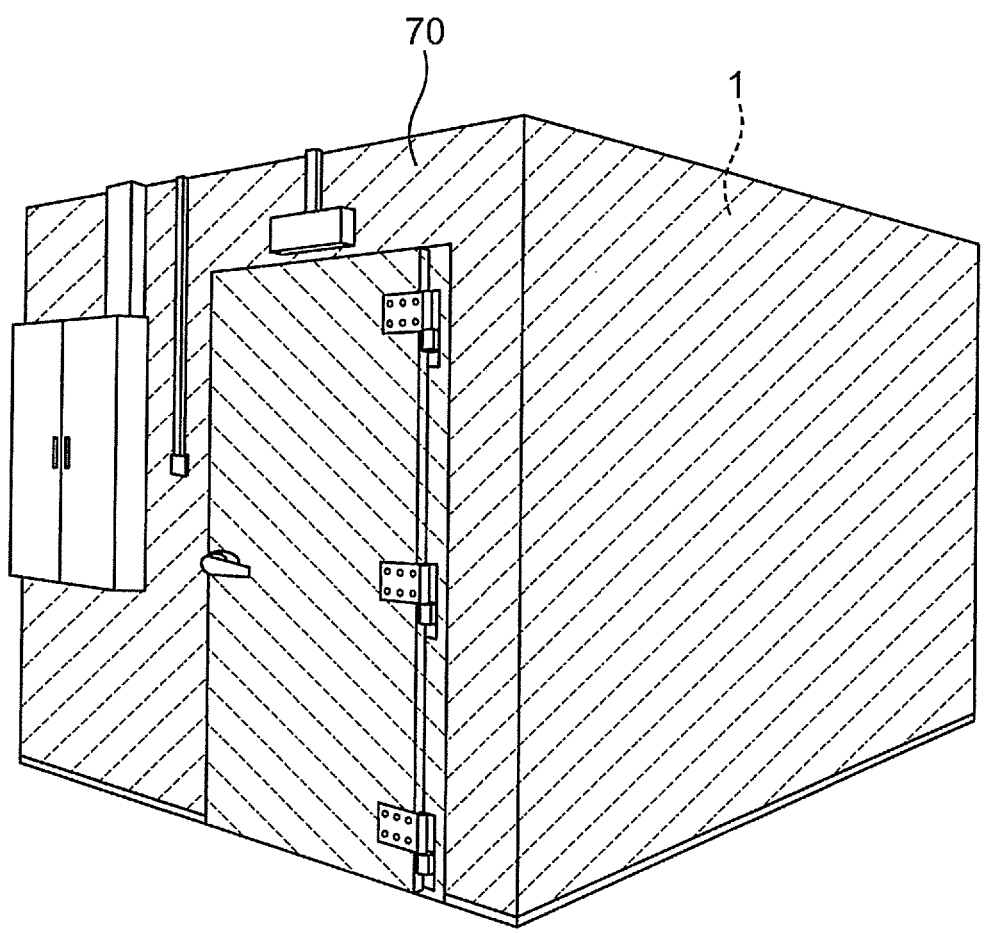
FIG. 16 is a perspective view showing an example in which building materials constituting a simplified shield room such as a wall, a ceiling, a floor, a door, or the like, may include the electromagnetic wave shielding material.

FIG. 16 is a perspective view showing an example in which building materials constituting (sealing or substantially sealing) a simplified shield room 70 such as a wall, a ceiling, a floor, a door, etc. include the electromagnetic wave shielding material 1. For example, when radio waves having a specific frequency are measured in the simplified shield room 70, the radio waves having the specific frequency entering inside from the outside of the simplified shield room 70 may make accurate measurement of the radio waves impossible.

In such a case, as shown in FIG. 16, the building materials of the simplified shield room 70 are configured to include the electromagnetic wave shielding material 1 configured to shield the radio waves having the specific frequency. As a result, the electromagnetic wave shielding material 1 can shield the radio waves having the specific frequency measured in the simplified shield room 70 so as to prevent the radio waves from entering inside from the outside of the simplified shield room 70.

Examples of use of the simplified shield room 70 include, for example, reading a UHF-band RFID tag in a component mounting process. For example, when a plurality of component mounting processes including the electromagnetic wave shielding material 1 are adjacently arranged and electromagnetic waves of a specific frequency are used in each of the component mounting processes, radio wave interference or a reading error of RFID tags can be prevented from occurring due to the electromagnetic waves used in the adjacent component mounting processes.

The shield room is normally required to be completely grounded, and installation locations are limited. In this regard, as described above, the electromagnetic wave shielding material 1 has a configuration in which the plurality of the electrically-closed resonance loops 3 are arranged like floating islands and therefore can suppress the reflection of the electromagnetic waves without grounding.

(Article with Electromagnetic Wave Shielding Material)

An article including the electromagnetic wave shielding material 1 (an article with an electromagnetic wave shielding material) will hereinafter be described. In this description, the article refers to a tangible object other than the building material. Examples of the article include a movable screen and an electronic device such as a mobile phone (smartphone) and a microwave oven.

Figure 17:
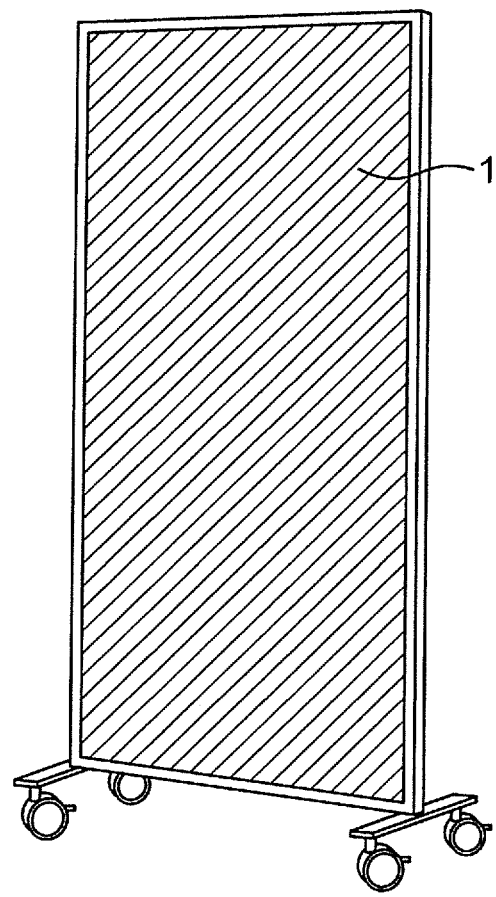
FIG. 17 is a perspective view showing an example in which a movable screen includes the electromagnetic wave shielding material.

FIG. 17 is a perspective view showing an example in which an exemplary article, i.e., a movable screen 80, includes the electromagnetic wave shielding material 1. For example, when radio waves having a specific frequency are measured in a plurality of regions close to each other, radio wave interference may occur.

In such a case, as shown in FIG. 17, the movable screen 80 is configured to include the electromagnetic wave shielding material 1 configured to shield the radio waves having a specific frequency. As a result, radio waves used in two regions with the movable screen 80 interposed therebetween are shielded by the electromagnetic wave shielding material 1, so that radio wave interference can be suppressed.

Figure 18:
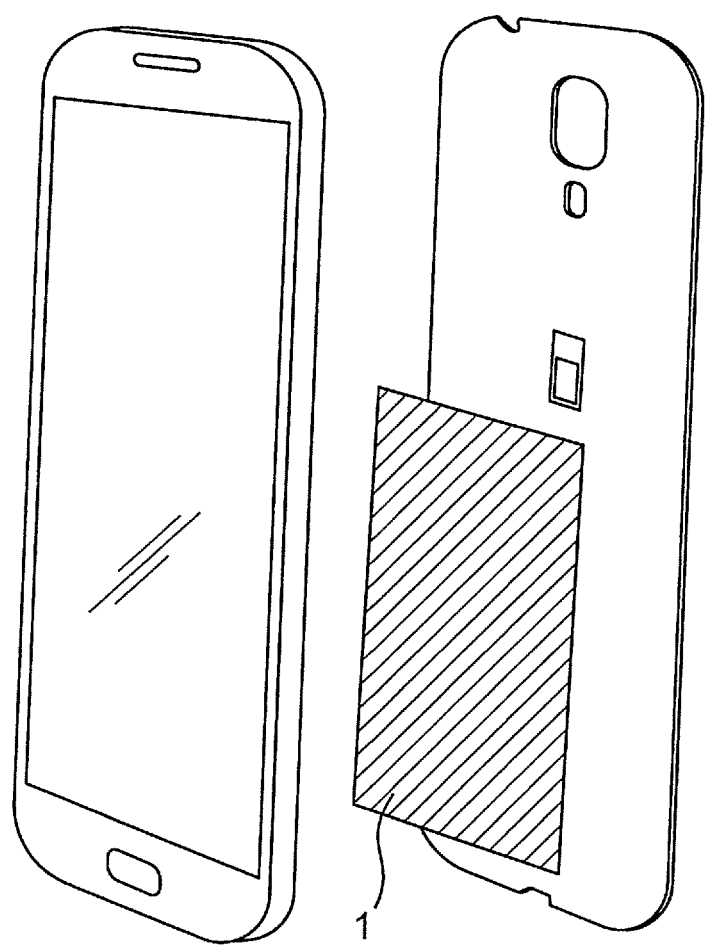
FIG. 18 is a perspective view showing an example in which a mobile phone includes the electromagnetic wave shielding material.

FIG. 18 is a perspective view showing an example in which an exemplary article, i.e., a mobile phone 90, includes the electromagnetic wave shielding material 1. The mobile phone 90 is normally provided with a ferrite sheet for preventing radio wave interference between components.

As shown in FIG. 18, the mobile phone 90 including the electromagnetic wave shielding material 1 instead of the ferrite sheet can prevent radio wave interference between components.

Although the present disclosure has been sufficiently described in terms of preferable embodiments with reference to the accompanying drawings, various modifications and corrections are apparent to those skilled in the art. It should be understood that such modifications and corrections are included in the present disclosure without departing from the scope of the present disclosure according to the accompanying claims.

The electromagnetic wave shielding material of the present disclosure can prevent usage environment from being limited and is therefore useful as an electromagnetic wave shielding material shielding electromagnetic waves of a specific frequency.

EXPLANATIONS OF LETTERS OR NUMERALS 1 electromagnetic wave shielding material
2 substrate
2a first principal surface
2b second principal surface
3 resonance loop
3A large-diameter resonance loop
3B small-diameter diameter resonance loop
21 first sheet member
22 second sheet member
31 first conductor
32 second conductor
33 capacitor element
50 wireless LAN
60 MRI apparatus
70 simplified shield room
80 movable screen
90 mobile phone

The invention claimed is:

1. An electromagnetic wave shielding material for shielding an electromagnetic wave having a frequency, comprising:
    a substrate including a first principal surface and a second principal surface opposite to the first principal surface; and
    a plurality of resonance loops disposed on the substrate, wherein the plurality of resonance loops are positioned on the substrate to be magnetically coupled to each other,
    wherein each of the resonance loops forms an LC parallel resonance circuit that is configured to resonate at the frequency of the electromagnetic wave, and
    wherein each of the resonance loops includes a first conductor formed on the first principal surface and a second conductor formed on the second principal surface, with the first and second conductors having respective portions that overlap each other in a direction orthogonal to at least one of the first and second principal surfaces, and
    wherein the respective first and second conductors of each resonance loop form a closed loop and are capacitively coupled to each other via the substrate.

2. The electromagnetic wave shielding material according to claim 1, wherein a length in an arrangement direction of the plurality of resonance loops is ½ wavelength or more at the frequency of the electromagnetic wave.

3. The electromagnetic wave shielding material according to claim 1, wherein each of the resonance loops is a minute loop having a perimeter less than ½ wavelength at the frequency of the electromagnetic wave.

4. The electromagnetic wave shielding material according to claim 1, wherein the substrate comprises a flexible sheet member.

5. The electromagnetic wave shielding material according to claim 1, wherein each of the resonance loops comprises a transparent electrode.

6. The electromagnetic wave shielding material according to claim 1,
    wherein the first and second conductors each are openended conductors that have respective portions that overlap each other to collectively form the closed loop.

7. The electromagnetic wave shielding material according to claim 1,
    wherein the substrate includes a first sheet member and a second sheet member laminated to each other, and
    wherein the plurality of resonance loops are disposed on each of the first sheet member and the second sheet member.

8. The electromagnetic wave shielding material according to claim 7, wherein the plurality of resonance loops have same inner and outer diameter dimensions and are disposed at regular intervals on the substrate, and wherein the first sheet member and the second sheet member are configured such that a plurality of resonance loops disposed on the first sheet member are shifted in a plane direction from a plurality of resonance loops disposed on the second sheet member.

9. The electromagnetic wave shielding material according to claim 1, wherein the plurality of resonance loops include:
a first resonance loop group comprising at least two or more resonance loops configured to resonate at a first frequency, and
a second resonance loop group comprising at least two or more resonance loops configured to resonate at a second frequency different from the first frequency.

10. The electromagnetic wave shielding material according to claim 9,
wherein the substrate includes a first sheet member and a second sheet member laminated to each other,
wherein the first resonance loop group is disposed on the first sheet member, and
wherein the second resonance loop group is disposed on the second sheet member.

11. The electromagnetic wave shielding material according to claim 1, wherein the LC parallel resonance circuit has a Q value of 1 or more and 30 or less.

12. A building material comprising:
an electromagnetic wave shielding material configured to shield an electromagnetic wave having a frequency, wherein the electromagnetic wave shielding material comprises:
a substrate including a first principal surface and a second principal surface opposite to the first principal surface, and
a plurality of resonance loops disposed on the substrate, with each resonance loop including a first conductor formed on the first principal surface and a second conductor formed on the second principal surface,
wherein the first and second conductors of each resonance loop have respective portions that overlap each other in a direction orthogonal to at least one of the first and second principal surfaces to form a closed loop, with the first and second conductors being capacitively coupled to each other via the substrate,
wherein the plurality of resonance loops are positioned on the substrate to be magnetically coupled to each other, and
wherein each of the resonance loops forms an LC parallel resonance circuit that is configured to resonate at the frequency of the electromagnetic wave.

13. The building material according to claim 12, wherein a length in an arrangement direction of the plurality of resonance loops is ½ wavelength or more at the frequency of the electromagnetic wave.

14. The building material according to claim 12, wherein each of the resonance loops is a minute loop having a perimeter less than ½ wavelength at the frequency of the electromagnetic wave.

15. The building material according to claim 12, wherein the substrate comprises a flexible sheet member.

16. The building material according to claim 12,
wherein the first and second conductors each are open-ended conductors that have respective portions that overlap each other to collectively form the closed loop.

17. An article comprising:
an electromagnetic wave shielding material configured to shield an electromagnetic wave having a frequency, wherein the electromagnetic wave shielding material comprises:
a substrate including a first principal surface and a second principal surface opposite to the first principal surface, and
a plurality of resonance loops disposed on the substrate and positioned thereon, such that the plurality of resonance loops are magnetically coupled to each other, with each resonance loop including a first conductor formed on the first principal surface and a second conductor formed on the second principal surface,
wherein the first and second conductors of each resonance loop have respective portions that overlap each other in a direction orthogonal to at least one of the first and second principal surfaces to form a closed loop, with the first and second conductors being capacitively coupled to each other via the substrate, and
wherein each of the resonance loops forms an LC parallel resonance circuit that is configured to resonate at the frequency of the electromagnetic wave.

18. The article according to claim 17, wherein a length in an arrangement direction of the plurality of resonance loops is ½ wavelength or more at the frequency of the electromagnetic wave.

19. The article according to claim 17, wherein each of the resonance loops is a minute loop having a perimeter less than ½ wavelength at the frequency of the electromagnetic wave.

20. The article according to claim 17,
wherein the first and second conductors each are open-ended conductors that have respective portions that overlap each other to collectively form the closed loop.

* * * * *